(12) United States Patent
Fontcuberta et al.

(10) Patent No.: US 7,459,706 B2
(45) Date of Patent: Dec. 2, 2008

(54) INSTALLATION AND METHOD FOR STERILISING OBJECTS BY LOW-ENERGY ELECTRON BOMBARDMENT

(75) Inventors: Philippe Fontcuberta, Vendome (FR); Didier Morisseau, Antony (FR); Arnaud Coupez, Saint Cheron (FR)

(73) Assignee: Linac Technologies SAS, Orsay (FR)

( * ) Notice: Subject to any disclaimer, the term of this patent is extended or adjusted under 35 U.S.C. 154(b) by 132 days.

(21) Appl. No.: 11/342,712

(22) Filed: Jan. 31, 2006

(65) Prior Publication Data

US 2006/0186350 A1      Aug. 24, 2006

(30) Foreign Application Priority Data

Feb. 1, 2005      (FR) .................................... 05 50287

(51) Int. Cl.
*A61N 5/00* (2006.01)
*H01J 37/20* (2006.01)
*A61L 2/00* (2006.01)

(52) U.S. Cl. .................. 250/492.3; 422/22; 250/455.11
(58) Field of Classification Search .............. 250/491.1, 250/492.1, 455.11, 492.3; 422/22
See application file for complete search history.

(56) References Cited

U.S. PATENT DOCUMENTS

| | | | |
|---|---|---|---|
| 4,599,216 A | | 7/1986 | Rohrer et al. |
| 5,252,290 A | * | 10/1993 | Uesugi ........................ 422/22 |
| 6,639,225 B2 | * | 10/2003 | Kirschstein et al. .... 250/442.11 |
| 2003/0091468 A1 | | 5/2003 | Buchanan |
| 2004/0245481 A1 | * | 12/2004 | Avnery ..................... 250/492.1 |
| 2005/0199807 A1 | * | 9/2005 | Watanabe et al. ........... 250/306 |
| 2006/0186350 A1 | | 8/2006 | Fontcuberta et al. |

FOREIGN PATENT DOCUMENTS

WO      WO 99/39750      8/1999

OTHER PUBLICATIONS

U.S. Appl. No. 11/911,161, filed Oct. 10, 2007, Fontcuberta, et al.

* cited by examiner

*Primary Examiner*—Jill Warden
*Assistant Examiner*—Kevin C Joyner
(74) *Attorney, Agent, or Firm*—Oblon, Spivak, McClelland, Maier & Neustadt, P.C.

(57) ABSTRACT

The invention relates to an installation (1) for sterilising objects (2) by low-energy electron bombardment, including sterilisation means (18) capable of generating an electron beam along an axis (A) passing through a treatment chamber (16). According to the invention, the installation includes a mechanical module (12) designed so as to be capable of generating a relative rotation movement, between the object and the sterilisation means, about an axis (A') chosen so that axis (A) of the electron beam generated by the sterilisation means continuously passes through the external surface of the object during the relative rotation movement about the axis (A'). In addition, it comprises mechanical module (22) enabling the object to be rotated about an axis (A") oriented orthogonally with respect to axis (A').

27 Claims, 6 Drawing Sheets

INSTALLATION AND METHOD FOR STERILISING OBJECTS BY LOW-ENERGY ELECTRON BOMBARDMENT

TECHNICAL FIELD

This invention relates in general to the field of sterilising objects by low-energy electron bombardment on the external surface of said objects.

It applies particularly but not exclusively to sterilisation by low-energy electron bombardment of objects having a substantially rectangular parallelepiped shape, such as objects called "tubs" corresponding to closed containers containing a multitude of elements that are preferably chemically pre-sterilised, such as medical syringes.

More specifically, the invention relates to an installation for sterilising objects by low-energy electron bombardment on the surface of said objects, as well as a sterilisation method capable of being implemented by such an installation.

PRIOR ART

The prior art includes installations for sterilising objects with a substantially rectangular parallelepiped shape by low-energy electron bombardment, i.e. with an energy lower than around 400 KeV.

To do this, these installations typically comprise three low-energy accelerator/gun-type sources of round 200 KeV, and are arranged at 120° with respect to one another around a treatment chamber through which the objects are moved translationally so as to be treated. In this way, as it continuously passes through the treatment chamber, the external surface of each object is simultaneously lighted over 360° by the combination of three electron beams from the aforementioned sources, which are carefully positioned.

This type of installation has proved to be satisfactory, in particular owing to its efficacy associated with the light penetration of the electron beam and the sporicidal effect produced, and also owing to its rapid treatment as well as the safety provided.

Nevertheless, this installation has a major disadvantage lying in the fact that it requires three distinct low-energy accelerator/gun-type sources in order to perform the sterilisation by irradiation of the entire external surface of each object. Obviously, this constraint associated with the necessary presence of three complex low-energy sources makes the installation extremely costly, and, therefore, it is not entirely optimised.

Moreover, it is noted that the particularly large space requirement of this installation also constitutes another disadvantage.

OBJECT OF THE INVENTION

The objective of the invention is therefore to propose an installation for sterilising objects by low-energy electron bombardment on the surface of said objects, as well as a sterilisation method capable of being implemented by such an installation, which installation and method at least partially overcome the disadvantages mentioned above with regard to the prior art.

To do this, the invention first relates to an installation for sterilising objects by low-energy electron bombardment on the external surface of said objects, which installation includes sterilisation means capable of generating a low-energy electron beam along an axis A passing through a treatment chamber of the installation. According to the invention, it also includes a first mechanical module designed so as to be capable of generating, during the sterilisation of an object to be treated located inside the treatment chamber, a relative rotation movement between the object and the sterilisation means, about an axis A' chosen so that axis A of the electron beam generated by the sterilisation means continuously passes through the external surface of the object during the relative rotation movement about said axis A'. In addition, the installation comprises a second mechanical module designed so as to be capable of generating, when the object located inside said treatment chamber is released from the first mechanical module, a rotation of the object about an axis A" oriented orthogonally with respect to axis A'.

In other words, one of the special features of the invention consists of establishing a relative rotation movement between the sterilisation means and the object, so that the external surface of the latter is treated continuously and progressively during said relative rotation movement.

In the installation according to the invention, it is advantageously no longer necessary to use three distinct low-energy sources intended to jointly and simultaneously light the external surface of an object over 360°. Indeed, with the proposed arrangement, the object to be sterilised can be treated using a single low-energy source of which the electron beam along axis A, at any time t of the relative rotation movement, lights only an angular section smaller than 360° of the external surface of the object. It is then the application of the relative rotation movement about axis A', continuously passing through the external surface of the object and preferably being orthogonal to axis A, that enables said external surface to be lighted and progressively treated over 360°.

Obviously, the requirement of only one low-energy accelerator/gun-type source leads to a significant reduction in the overall cost as well as a reduced space requirement by comparison with the installations known from the prior art.

The installation according to the invention is preferably designed so that each object to be sterilised is handled automatically during its entire passage between a conveyor located at the inlet of the installation, and a production isolator located at the outlet of this installation.

It is thus noted that the installation is suitable for receiving a plurality of objects moving continuously on the inlet conveyor, with each of them being intended to successively enter the treatment chamber. The installation is preferably intended to operate at a so-called "low" rate on the order of 1 object/minute, corresponding for example to 30 seconds of transfer between the inlet and the outlet of the installation, and 30 seconds of actual treatment by electron bombardment in order to sterilise the external surface of the object.

The installation according to the invention, for which the electron beam generated by the sterilisation means continuously lights the object during the relative rotation movement along axis A', is naturally suitable for treating objects of any shape, including the preferred "tub", for example, for medical syringes, substantially having the shape of a rectangular parallelepiped. Of course, other shapes of objects to be sterilised at the surface can be considered, such as a cylindrical shape with a circular cross-section, without going beyond the scope of the invention.

In addition, it is noted that the installation is naturally designed so as to ensure regulation of the air flow through the treatment chamber during the phases in which the object is transferred into the installation.

Moreover, by applying such a rotation about axis A" as mentioned above, it becomes possible, after having scanned the surface over 360° using the first mechanical module and around axis A', to consider treating the surfaces of the object that were not treated during the first rotation about axis A'. This special feature is particularly advantageous when the installation is intended for sterilising objects having a substantially rectangular parallelepiped shape, such as tubs.

The first mechanical module is preferably controlled so as to cooperate, during the sterilisation of the object to be treated located inside said treatment chamber, with any one of the two elements selected from the object and the sterilisation means, so as to rotate this element about axis A'. In this way, it should be understood that, although the aforementioned relative rotation movement is preferably obtained by applying a rotation to the object while the sterilisation means are kept stationary on the installation, the reverse can clearly be considered.

As mentioned above, the installation is preferably designed so that the object to be treated constitutes the element intended to cooperate with the first mechanical module as to be rotated about axis A', and the sterilisation means are then mounted stationarily on the installation.

In such a case, it is possible for the first mechanical module to be provided with means for gripping the object to be treated, which first module comprises first movement means intended to bring the object, cooperating with the gripping means, into the treatment chamber so that a first surface of this object is passed through by axis A, preferably perpendicularly. In addition, the first mechanical module also includes second movement means designed so as to rotate the object and the gripping means about axis A' oriented orthogonally with respect to axis A and with respect to a second surface of the object, with the second mechanical module including third movement means designed so to rotate the object released from the gripping means approximately 90°, inside the treatment chamber, about axis A" oriented orthogonally with respect to axis A' and with respect to any one of the surfaces of the object which are perpendicular to the aforementioned second surface.

With such a configuration having first and second mechanical modules which have just been described, the installation is entirely suitable for sterilising the six surfaces of a rectangular parallelepiped object, as will be described in detail below.

The second mechanical module preferably comprises fourth movement means designed so as to move the object in translation according to axis A", so as to separate it from said gripping means during its rotation of approximately 90° about this same axis A", generated by the third movement means. Of course, these fourth means also make it possible to bring the object toward the gripping means, after said rotation has been performed. In this regard, it is noted that the first mechanical module is designed and controlled so that its gripping means re-engage the object having a substantially rectangular parallelepiped shape subjected to the rotation of approximately 90° generated by the third movement means, so that the object can be rotated about axis A' by the second movement means. Naturally, this second rotation about axis A' is basically intended to sterilise the two parallel surfaces of the parallelepiped object that were not treated during the first 360° rotation about this same axis. Nevertheless, it can optionally be used to complete the treatment of the other two surfaces already sterilised during the first rotation, but also lighted by the electron beam during the second rotation of the object about said axis A'.

Also preferably, axis A" is oriented in the direction of the height Z of the installation, and axis A is oriented in the direction of the forward movement of the objects X in the installation, with directions X and Z being mutually orthogonal. In this regard, axis A is also preferably oriented in the direction of the height Z.

The installation also includes an inlet lock and an outlet lock having therebetween the treatment chamber communicating with said locks, which treatment chamber as well as the two inlet and outlet locks are aligned in direction X. In such a case, the first movement means are designed so as to enable a translation movement in direction X of the object held by the gripping means, between the inlet lock and the treatment chamber, and between said treatment chamber and the outlet lock.

Preferably, the two inlet and outlet locks in closed position and the treatment chamber jointly form an unsealed, shielded enclosure, which therefore allows for total biological protection from the electron beam, but which is still capable of allowing air to pass through, in particular at the level of the closures of the two locks.

Each of the two inlet and outlet locks is preferably associated with an elevator oriented in direction Z, which enables the space requirement of such an installation to be reduced considerably. Moreover, each of the two elevators comprises a shielded mobile plate serving as a carrier for the object, which plate is designed so as to ensure the closure of the lock with which it is associated, and therefore constitutes a portion of the unsealed, shielded enclosure mentioned above.

In addition, the two elevators cooperate respectively with an inlet conveyor and an outlet conveyor, each being capable of moving objects. Thus, the outlet conveyor leads to a production isolator into which the sterilised objects are delivered.

In addition, the invention also relates to a method for sterilising objects by low-energy electron bombardment on the external surface of said objects, which method has the special feature of being implemented by an installation such as that described above.

In other words, this method generally involves, after brining an object to be treated into the treatment chamber, of applying, by means of the first mechanical module, a movement of relative rotation between the object and the sterilisation means, about an axis A' chosen so that axis A of the electron beam generated by the sterilisation means continuously passes through the external surface of the object during this relative rotation movement about said axis A'.

Other advantages and features of the invention will appear in the following non-limiting detailed description.

BRIEF DESCRIPTION OF THE DRAWINGS

This description will be provided with regard to the appended drawings in which.

DETAILED DESCRIPTION OF PREFERRED EMBODIMENTS

Figure 1:
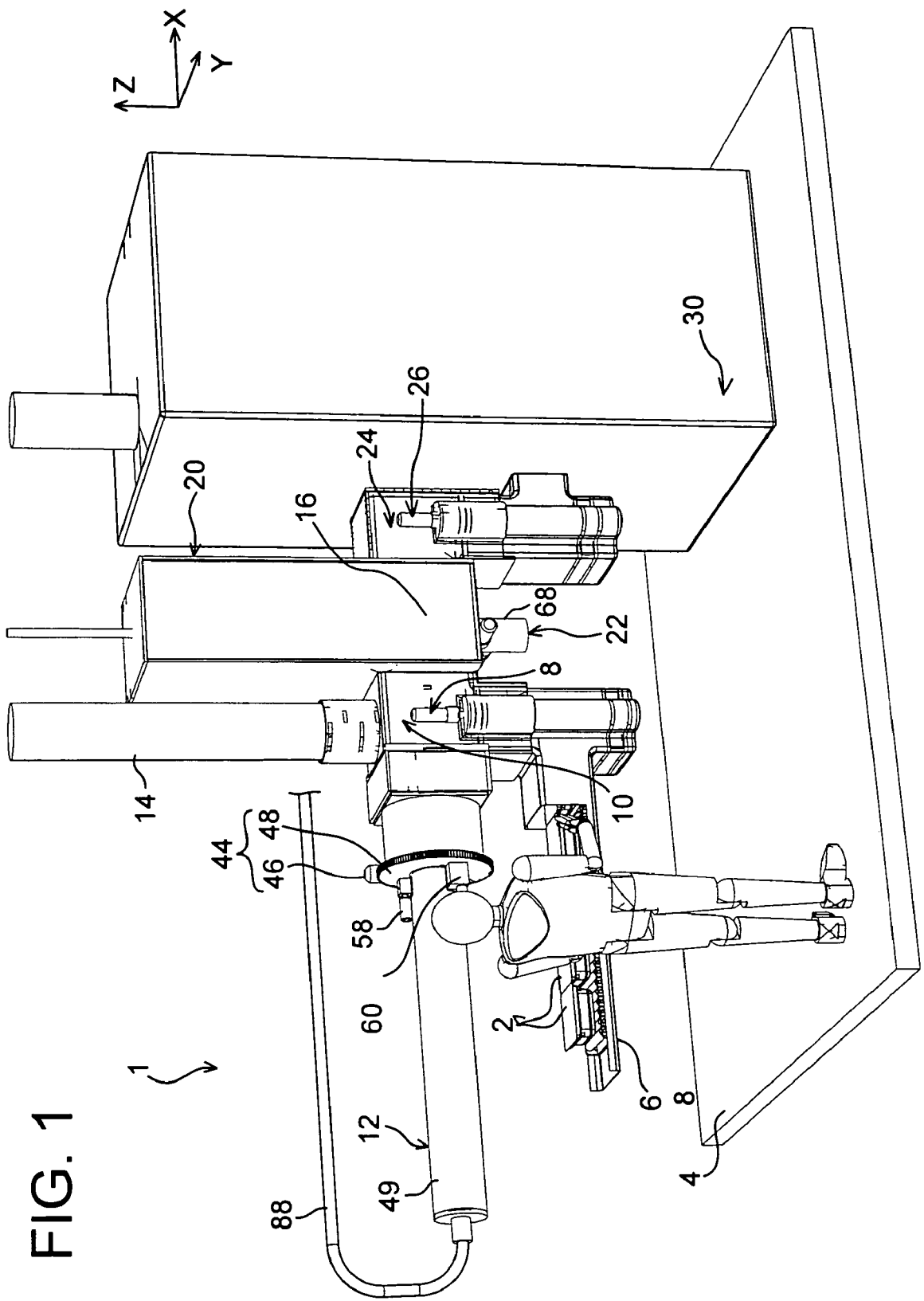
FIG. 1 shows a perspective view of an installation for sterilising objects by low-energy electron bombardment, according to a preferred embodiment of the present invention.
Figure 2:
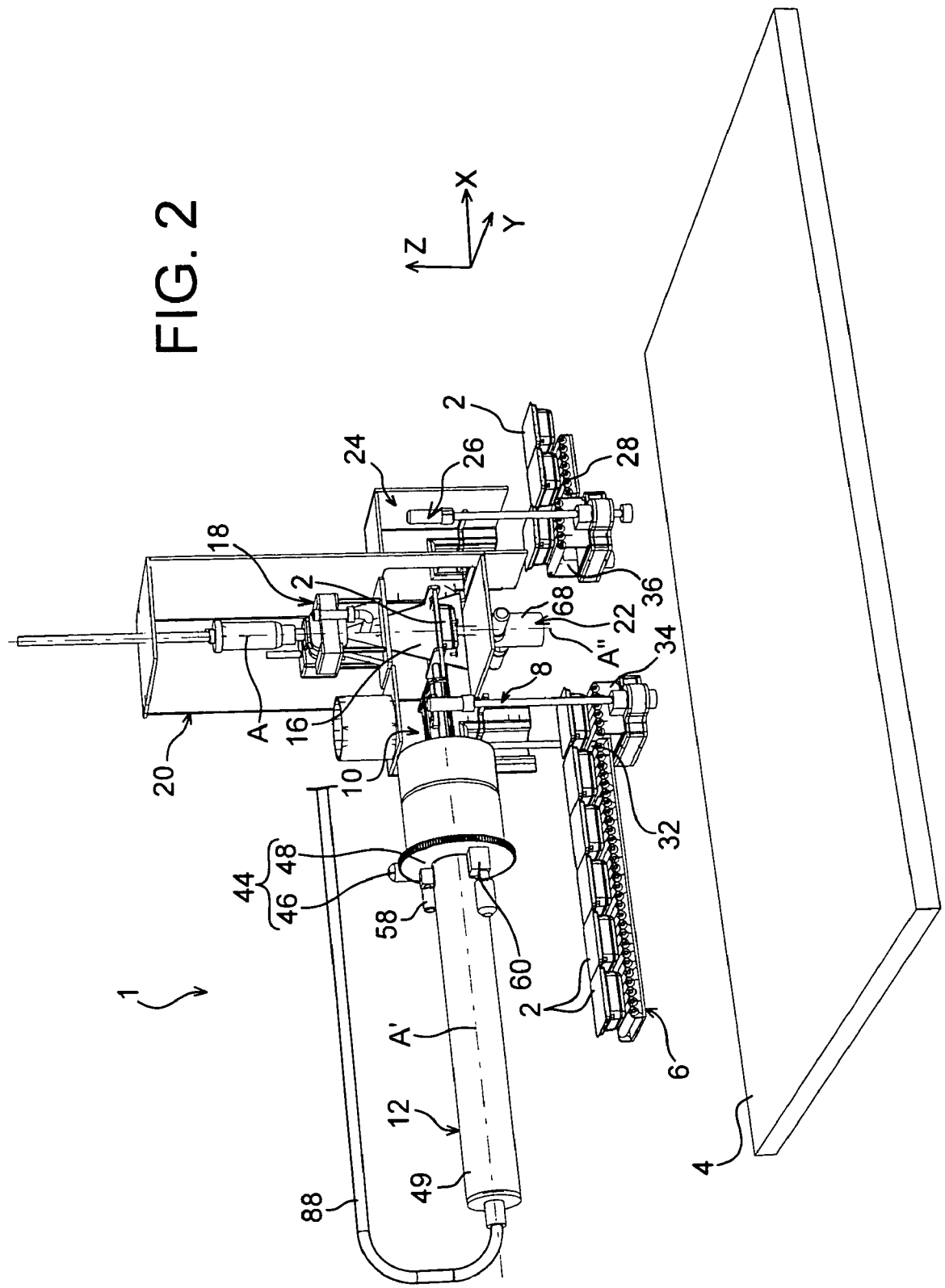
FIG. 2 shows a view similar to that of FIG. 1, in a version in which some elements of the installation have been voluntarily omitted, for the sake of clarity

In reference first to both FIGS. 1 and 2, an installation 1 for sterilising objects 2 by low-energy electron bombardment can be seen, which installation 1 is intended in particular for treating objects having a substantially rectangular parallelepiped shape.

As mentioned above, this shape corresponds in particular to that of tubs containing a multitude of elements, for example, one hundred per tub, which elements are preferably chemically pre-sterilised, such as medical syringes.

The installation 1 is placed on a floor 4, which can be characterised as a horizontal plane. It can thus be noted that the description will be provided in reference to a direction X parallel to the ground 4 and corresponding to a direction of forward movement of the objects in the installation, a direction Y corresponding to a transverse direction of the installation also parallel to the ground 4, as well as a direction Z corresponding to a direction of the height which is orthogonal to said ground 4, with directions X, Y and Z being mutually orthogonal.

In general, the installation comprises the following elements: an inlet conveyor 6, an inlet elevator 8, an inlet lock 10, a first mechanical module 12 for moving objects 2, an ozone discharge pipe 14, a treatment chamber 16 also called a "firing tunnel", sterilisation means 18 located inside a casing 20, a second mechanical module 22 for moving objects 2, an outlet lock 24, an outlet elevator 26, an outlet conveyor 28, and a production isolator 30 into which the sterilised objects 2 are delivered.

The inlet conveyor 6 is a wheeled gravity conveyor moving objects 2 to be treated, substantially in direction X. It is equipped with a gate 32 in the low portion, controlled by an electromagnet (not shown) or by another type of actuator known to a person skilled in the art, and enabling the objects 2 to be released one by one so that they successively and automatically enter the inlet elevator 8 by gravity. As can be seen in FIG. 1, the end portion of the inlet conveyor 6 is surrounded by a protective wall, preferably made of stainless steel, which wall extends into a low portion of the inlet elevator 8.

The inlet elevator 8 is also provided with a protective double-wall in its upper portion, which is comprised of an impervious coating of stainless steel, as well as a shielded coating preferably made of lead. As for the other shielded elements of the installation 1, the shielded coating surrounding the elevator 8 serves primarily to provide total biological protection from the electron beam emitted by the sterilisation means 18 during the treatment.

In addition, the elevator 8 has a shielded mobile plate 34 serving as a carrier for an object 2 from the conveyor 6, which plate 34 is capable of being moved in direction Z. It is noted that in the low position, the plate 34 is located substantially in the extension of the inlet conveyor 6, in direction X.

To the right of the elevator 8 in direction Z, i.e. upward, is the inlet lock 10 defined by a protective double-wall in the form of a parallelepiped box open toward the treatment chamber 16, which is adjacent in direction X. This protective double-wall is also comprised of an impervious stainless steel, as well as a shielded coating preferably made of lead, having a thickness on the order of 15 mm.

The first mechanical module 12 is mounted stationarily on an external surface YZ of said box, i.e. oriented in a plane defined by directions Y and Z, while the ozone discharge pipe 14 is mounted on a surface XY above this same box, i.e. oriented in a plane defined by directions X and Z. In this regard, it is specified that the shielded plate 34, in the high position, is intended to constitute a lower surface XY of the protective box mentioned above, of which an internal surface YZ has voluntarily been omitted so as to allow for communication between the inlet lock 10 and the adjacent treatment chamber 16. Thus, the plate 34, according to its position, is capable of ensuring the opening and closing of the inlet lock 10 equipped with the biological protection described above.

The treatment chamber 16 is located in the extension of the inlet lock 10 in direction X, and is also defined by a protective double-wall substantially in the form of a parallelepiped box open on each side in this same direction X. Here, again, the protective double-wall is comprised of an impervious coating of stainless steel, as well as a shielded coating preferably made of lead, having a thickness on the order of 15 mm. It is nevertheless noted that the upper surface XY of this box, i.e. oriented in a plane defined by directions X and Y, has only one impervious coating on which the sterilisation means 18 are arranged. These means are also located inside the shielded casing 20 made of lead on a thickness of around 15 mm, and arranged above the aforementioned box defining the treatment chamber 16.

The sterilisation means 18 capable of generating a low-energy electron beam along an axis A preferably take the form of an electron gun or accelerator having an energy level below 400 KeV, and for example on the order of 200 KeV. This gun 18 is therefore mounted stationarily on the installation 1 at the edge of the treatment chamber 16, and preferably adjacently in direction Z as can be seen clearly in FIG. 2. Thus, they are capable of emitting an electron beam along an axis A passing through the treatment chamber 6 and oriented parallel to direction Z. In addition, these sterilisation means 18 can, in a known manner, include at the end of the gun an electron beam scanning horn (not shown), which defines an outlet window for the electrons and is preferably oriented according to direction X.

The second mechanical module 22, which will be described in detail below, is mounted on a surface XY inside the aforementioned box.

The outlet lock 24 is located in the extension of the treatment chamber 16 in direction X, and is also defined by a protective double-wall in the form of a parallelepiped box open toward the treatment chamber 16. This protective double-wall is comprised of an impervious coating of stainless steel, as well as a shielded coating preferably made of lead, having a thickness on the order of 15 mm.

To the right of the outlet lock 24 in a direction opposite direction Z, i.e. downward, is the outlet elevator 26 which is also provided with a protective double-wall in its upper portion, comprised of an impervious coating of stainless steel, as well as a shielded coating preferably made of lead.

In addition, the elevator 26 has a shielded mobile plate 36 serving as a carrier for an object 2 from the outlet lock 24, which plate 36 is capable of moving in direction Z. In this regard, it is specified that the shielded plate 36, in the high position, is intended to constitute a lower surface XY of the protective box defining the outlet lock 24, of which an internal surface YZ has voluntarily been omitted so as to allow for communication between the inlet lock 24 and the adjacent treatment chamber 16. Thus, the plate 36, according to its position, is capable of ensuring the opening and closing of the outlet lock 24.

In addition, it is noted that in the low position, the plate 36 is located substantially in the extension of the outlet conveyor 28, in direction X. Like the inlet conveyor 6, the outlet conveyor 28 is a wheeled gravity conveyor moving objects 2 to be treated, substantially in direction X. As can be seen in FIG. 1, the initial portion of the outlet conveyor is surrounded by a protective wall, preferably made of stainless steel, which wall extends into a low portion of the outlet elevator 26.

Finally, it is noted that the outlet conveyor 28 leads into the production isolator 30.

Now, in reference to FIGS. 3 and 4, the first mechanical module 12 will be described.

In general, this first mechanical module 12 comprises means 38, 40 for gripping the object 2 to be treated, first movement means 42 intended to move said object 2 in translation inside the installation 1 according to an axis A' oriented in the direction X and therefore orthogonal to axis A, as well as second movement means intended to move said object 2 in rotation inside the installation 1, about said same axis A'. It is noted that these second means are shown only in FIGS. 1 and 2, where they are denoted with reference number 44. Indeed, these second means 44 are intended to turn the entire assembly shown in FIG. 3, by means of a drive pinion 46 and a gear assembly 48 of which the axis merges with axis A', mounted externally with respect to the shielded enclosure formed jointly by the locks 10, 26 and the treatment chamber 16. In addition, also in reference to FIG. 1, the first module 12 comprises an impervious, shielded protective double-wall 49 in the form of a casing having a circular cross-section, in which the assembly shown in said FIG. 3 is inserted.

Figure 4:
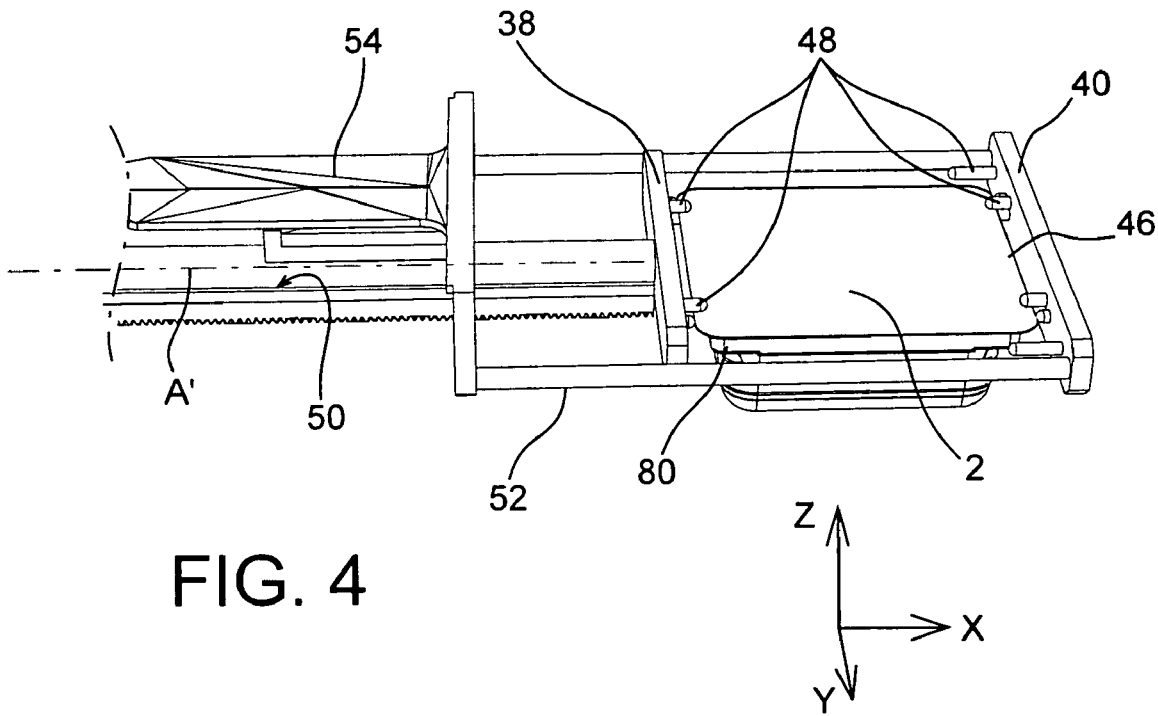
FIG. 4 shows a partial, enlarged perspective view of FIG. 3, more specifically showing the gripping means of the first mechanical module.

The gripping means have two parallel gripping surfaces 38 and 40, oriented substantially according to planes YZ, and each provided with teeth 49 extending in direction X so as to engage a circumferential edge 47 of the object 2, as can be seen in FIG. 4. Given that the gripping means are intended to hold the object 2 to be treated during the rotation thereof about axis A', these teeth 49 are of course distributed so as to be located above and below the aforementioned circumferential edge 46.

Figure 3:
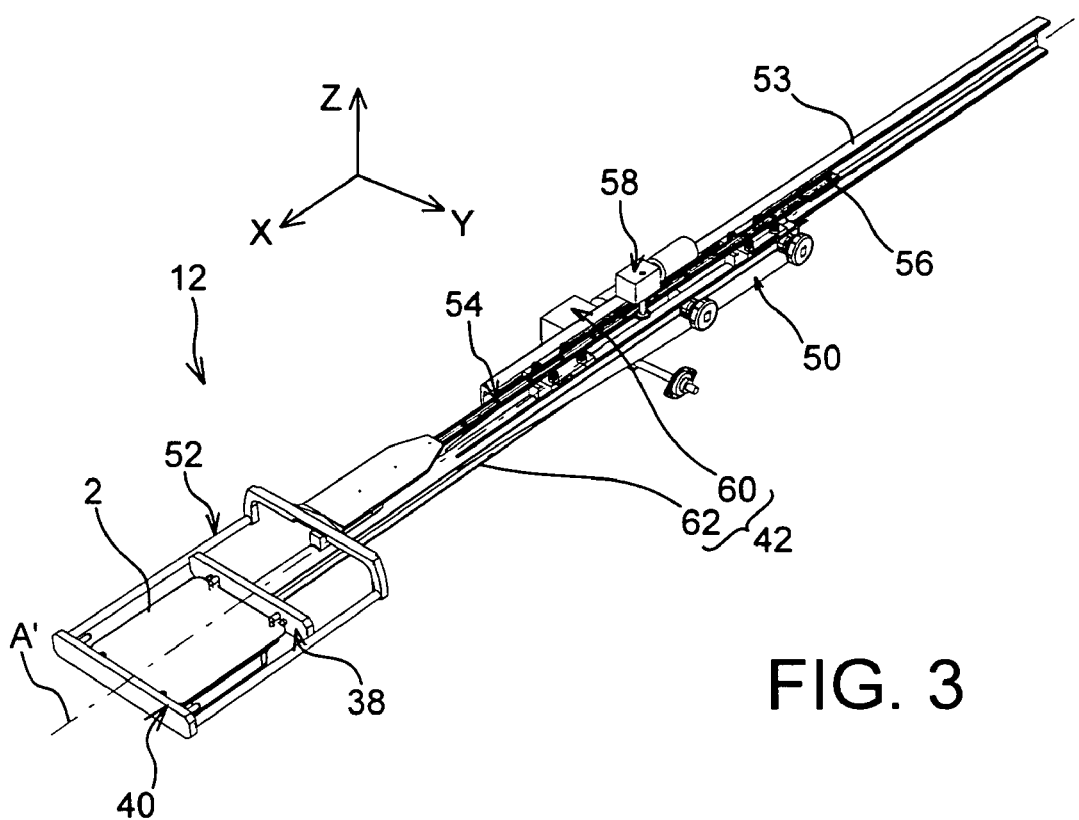
FIG. 3 shows a perspective view of a portion of the first mechanical module of the installation shown in FIG. 1.

The surface 38 is arranged at the end of a primary arm 50 of the first mechanical module 12, which arm 50 extending in direction X is intended to slide in this same direction along two parallel tracks 53 of which only one is shown in FIG. 3, for obvious reasons of clarity. In addition, the most external surface 40 belongs to a frame 52 arranged at the end of a secondary arm 54 of the first mechanical module 12, which frame 52 has a size large enough to be capable of being passed through by an object 2 in direction Z. In addition, the arm 54 also extends in direction X and is intended to slide in direction X with respect to the primary arm 50 above which it is preferably arranged. This option is provided by the presence of a rack 56 on the secondary arm 54, which is controlled by a drive pinion 58. Thus, by actuating this drive pinion 58, it is possible to control the distance in direction X between the two gripping surfaces 38, 40, primarily so as to adjust this same distance with respect to the size of the object 2 to be held.

Also in reference to said FIG. 3, it can be seen that the first movement means 42 intended to enable the sliding of the primary arm 50 on which the secondary arm 54 is supported, include a drive pinion 60 and a rack 62 arranged on this same arm 50.

As for the drive pinion 46 of the first mechanical module 12, the motors of the drive pinions 58 and 60 of this module are arranged outside the shield of the installation, as can be seen in FIGS. 1 and 2.

Figure 5:
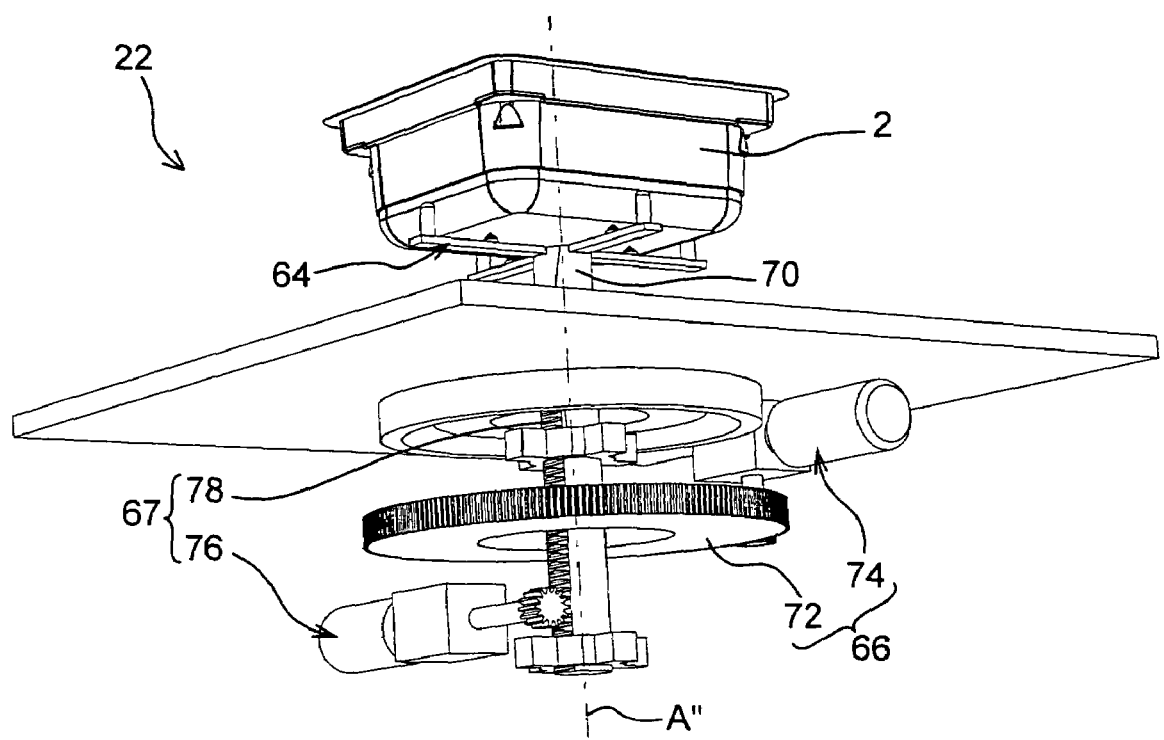
FIG. 5 shows a perspective view of the second mechanical module of the installation shown in FIG. 1.

In reference to FIG. 5, the second mechanical module 22 will be described.

In general, this second mechanical module 22 comprises means 64 for supporting the object 2 to be treated, third movement means 66 intended to move the object 2 in rotation inside the installation 1 about an axis A" oriented in direction Z, and preferably merging with axis A of the electron beam, and fourth movement means 67 intended to move the object 2 in translation inside the installation 1 according to said axis A". In addition, it can be seen in FIG. 1 that the second module 22 comprises an impervious, shielded protective double-wall 68 in the form of a casing having a circular cross-section, in which the assembly shown in said FIG. 5 is inserted.

The module 22 has an arm 70 oriented along axis A", and at the upper end of which are support means 64 on which the object 2 is capable of resting by gravity. In addition, this arm 70 is coupled to the third movement means 66 including a gear assembly 72 mechanically connected to this arm 70, which shares an axis with axis A" and cooperates with a drive pinion 74 also belonging to the third means 66. The elements 72, 74 are preferably arranged outside the shield of the installation, and more specifically that provided by the protective double-wall 68.

In addition, the fourth movement means 67 include a drive pinion 76 of which the motor is also provided outside the shield provided by the protective double-wall 68, which drive pinion 76 cooperates with a rack formed directly on the arm 70 so as to allow the latter to slide in direction Z.

The operation of the installation 1 during the implementation of a method for sterilising objects by low-energy electron bombardment, according to a preferred embodiment of the present invention, will now be described.

First, it is noted that all of the operations presented below can be automated with appropriate computer means (not shown), so that an operator need only manually place the objects 2 to be sterilised on the inlet conveyor 6, before each of them is handled entirely automatically during its entire passage between this same conveyor 6 and the production isolator 30.

The actuation of the gate 32 causes an object 2 to be released from the inlet conveyor 6, which can then automatically enter the inlet elevator 8 by gravity, and more specifically slide on the plate 34 held in the low position.

Then, the plate 34 is elevated to a high position in which it closes the inlet lock 10, and in which the object 2 supported by said plate 34 has penetrated the two surfaces 38, 40 of the gripping means, of which the separation has consequently been fixed. The drive pinions 58 and 60 are actuated so that the surfaces 38, 40 come together, and their teeth 49 respectively engage the circumferential edge 47 of two opposite surfaces of the object 2 oriented in parallel planes YZ, with a so-called second surface being indicated by reference 80 in FIG. 4.

This second surface 80 is therefore arranged orthogonally with respect to axis A', and is preferably passed through by the latter.

Then, the plate 34 is lowered slightly while ensuring continuous biological lead protection, and the first movement means 42 are actuated so as to move the object 2 in translation in direction X, toward the treatment chamber 16, by movement of the primary arm 50 in the same direction. The drive pinion 60, generating this movement in which drive pinion 58 obviously remains inactive, stops when an upper surface of the object 2 oriented in a plane XY is passed through orthogonally by axis A', and preferably in the middle. This upper so-called first surface is indicated by reference 82 in FIG. 4.

Figure 6A:
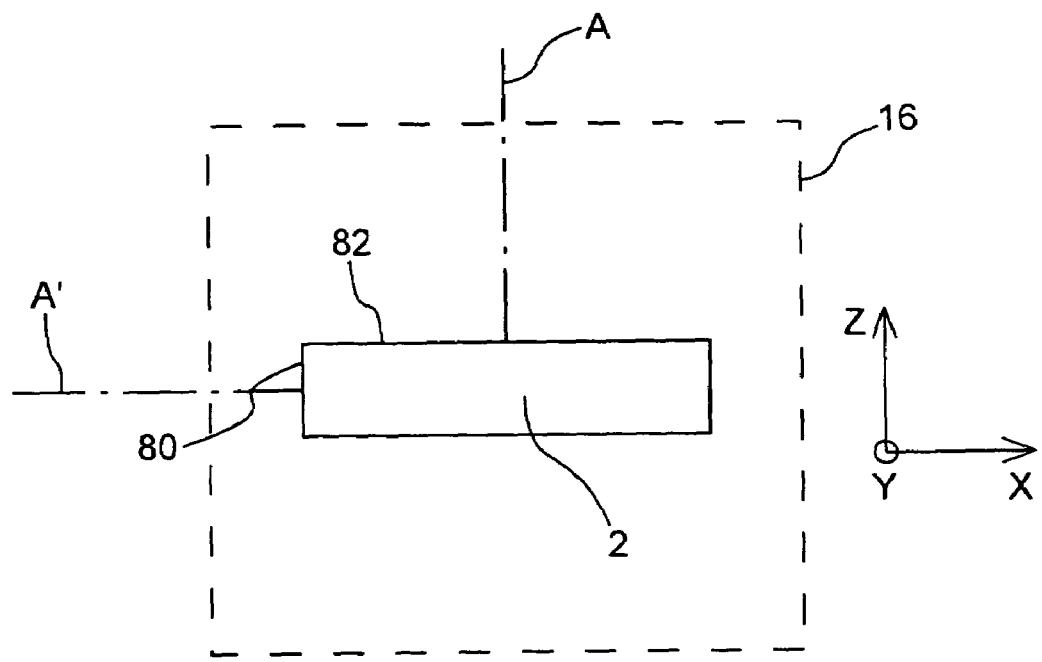
FIGS. 6a and 6b show front views diagramming the position of the object at different stages of its treatment in the installation.

At this time, the object 2 to be treated by electron bombardment at the surface is located inside the treatment chamber 16, as shown diagrammatically in FIG. 6a. The plate 36 of the elevator 26 is in the high position so as to close the outlet lock 24 in an unsealed manner, so that said lock, jointly with the inlet lock 10 and the chamber 16, constitutes an unsealed, shielded enclosure, providing total biological protection from the electron beam. The unsealed closure of the inlet lock 10 and the outlet lock 24 enables air to be supplied to the aforementioned enclosure, which is useful for diluting the ozone produced by the electron bombardment and intended to be discharged by the pipe 14. Moreover, this sealed closure results in a direction of air circulation favourable for the aseptic protection of the isolator 30.

At this stage, the sterilisation means 18 are then implemented so as to generate the aforementioned electron beam along axis A, so that the focal spot of said beam is fixed and can light substantially the entire surface of the first side 82, or so that a scanning of the beam with a lower focal spot is applied in direction X. Indeed, in this latter case, the oscillation frequency applied is high enough for the beam to light the entire surface of the object to be treated at the rotation speed applied.

Simultaneously, the second movement means 44 of the first mechanical module 12 are actuated by means of the drive pinion 46, so as to move the object 2 in rotation about axis A'.

This phase of rotating the object 2 about axis A', during which axis A of the fixed electron beam continuously passes through one of the surfaces of the object 2, is applied until said object has made a complete rotation, that is, until the entire first mechanical module 12 shown in FIG. 3 has performed a 360° rotation about said axis A'.

Thus, during this first phase of rotating the object 2, four of the six surfaces of said object are capable of being treated by low-energy electron bombardment, including the first surface 82. In addition, each of these four surfaces will have been exposed perpendicularly to axis A of the beam.

Naturally, to obtain a satisfactory treatment, it is possible to control the supply current/power of the sterilisation means 18, so that at the end of this first rotation phase, each of the four surfaces has a substantially identical and uniform unit dose. This desire to vary the power of the electron beam during the rotation of the object 2 about axis A' is of course motivated by the fact that these surfaces are exposed to the electron beam at a substantially long distance from the sterilisation means 18. Indeed, by way of example, the vertical distance between the base 55 of the sterilisation means 18 and the external surface of the treated object 2 can vary between 85 mm and 215 mm during the rotation. It is noted that, alternatively, the dose received by the object may also be regulated by controlling the position of the sterilisation means 18 with respect to that of the object 2 to be treated.

After the first rotation phase, the object 2 therefore returns to its initial position as shown in FIG. 6a. At this time, the fourth movement means 67 of the second mechanical module 22 are actuated so as to move the support means 64 in direction Z, until the latter come into contact with the lower surface of the object 2.

The drive pinions 58 and 60 are then actuated so that the surfaces 38, 40 separate from one another, and their teeth 49 release the circumferential edge 47 of the object 2. Once this operation has been completed, the object 2 is again moved in direction Z by the fourth movement means 67, so that this same object is sufficiently far from the gripping means 38, 40 and the frame 52 to be capable of being rotated about axis A" without hindrance.

In fact, the third movement means 66 are actuated by means of the drive pinion 74, in order to rotate the object 2 at an angle of 90° about said axis A", or optionally 270°.

Then, the fourth movement means 67 are again urged so as to bring the object 2 back down to a position enabling it to cooperate with the gripping means 38, 40, which are also then brought back toward one another so that their teeth 49 respectively engage the circumferential edge 47 of two other surfaces of the object 2. When this is achieved, the support means 64 are moved downward by means of the drive pinion 76 into their original resting position, in which they present no hindrance to the object 2 rotating about axis A'.

Figure 6B:
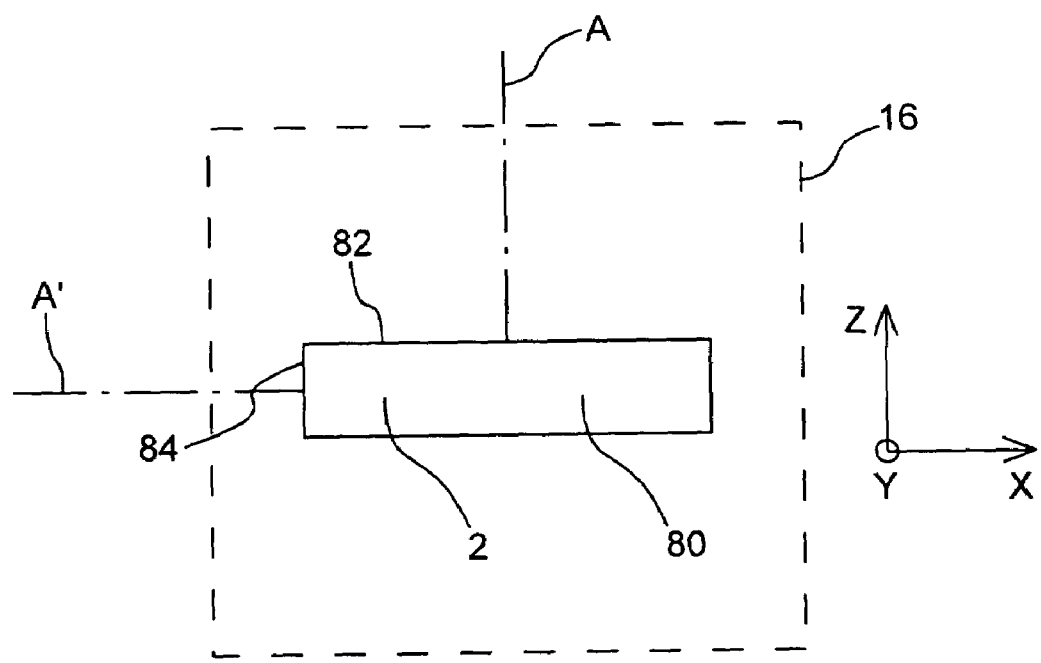

As can be seen in FIG. 6b, it is therefore one of the two surfaces orthogonal to the first and second surfaces 82, 80 that is orthogonally passed through by axis A', which so-called third surface is indicated by reference 84 in FIG. 6b. In addition, the first surface 82 remains the upper surface oriented in a plane XY, and is still orthogonally passed through by axis A of the electron beam.

The second movement means 44 of the first mechanical module 12 are again actuated by means of a drive pinion 46, so as to move the object 2 in rotation about axis A'.

This second phase of rotating the object 2 about axis A', during which axis A of the fixed electron beam continuously passes through one of the surfaces of the object 2, is preferably applied until said object has made a complete rotation.

Thus, during this second phase of rotating the object 2 about axis A', four of the six surfaces of said object are capable of being treated by low-energy electron bombardment, including the first surface 80 and that parallel to and opposite it (not shown), which two surfaces are the only ones not to have been treated during the first rotation phase.

Here, again, it is noted that to obtain a satisfactory treatment, it is possible to control the supply current/power of the sterilisation means 18, so that at the end of this second rotation phase, each of the four surfaces has a substantially identical and uniform unit dose. The alternative in which the position of the sterilisation means 18 can be controlled with respect to the position of the object 2 to be treated can also be considered. By way of indication, as two of the surfaces have already been treated in the first object rotation phase, the control can be implemented so that the treatment of these two surfaces constitutes only a minimal complementary treatment with respect to that already performed in the first rotation phase. Nevertheless, other solutions can naturally be considered for ensuring the sterilisation of the two surfaces passed through by axis A during each of the two rotation phases, such as, for example, the solution in which half of the treatment is provided during each of said two rotations, or the solution in which the entire treatment required is provided during only one of these two phases.

At the end of the second rotation phase, also marking the end of the lighting of the object 2 by the sterilisation means, the object is returned to the position shown in FIG. 6b, before being moved in direction X by the first movement means 42. This translation is stopped when the object 2 arrives at the outlet lock 24, and is located to the right and almost in contact with the plate 36 of the outlet elevator 26.

The drive pinions 58 and 60 are then actuated so that the surfaces 38, 40 separate from one another, and their teeth 49 release the circumferential edge 47 of the object 2. The object 2 moved by the elevator 24 in a direction opposite direction Z, i.e. downward, is stopped when the plate 36 reaches a low position where said object 2 is automatically transferred by gravity to the outlet conveyor 28 which brings it to the production isolator 30.

It is specified that the method is preferably implemented so that during the phase in which the treated object 2 is lowered on the plate 36, said object 2 begins its course in the installation 1, for example by being moved by the inlet elevator 8 to the inlet lock 10.

Finally, it is indicated that a prior sterilisation of the installation 1 can be performed by closing the lock 10 with the plate 34, and by circulating a sterilising agent from the isolator 30 through the unsealed, shielded enclosure, which agent is capable of being discharged through a conduit 88 mounted at a free end of the protective double-wall, in the form of a casing 49, of the first mechanical module 12, as well as by the pipe 14. During this phase of sterilising the installation 1, it is noted that the plate 34 is brought to a position enabling it press against a sealing joint (not shown) provided around the opening of the inlet lock 10, so that, unlike what is sought during the sterilisation of the objects 2 by electron bombardment, the inlet lock 10 is hermetically sealed. During the operation of sterilising the installation 1, the sterilising agent then circulates in a direction going from the isolator 30 to the inlet lock 10.

Figure 7:
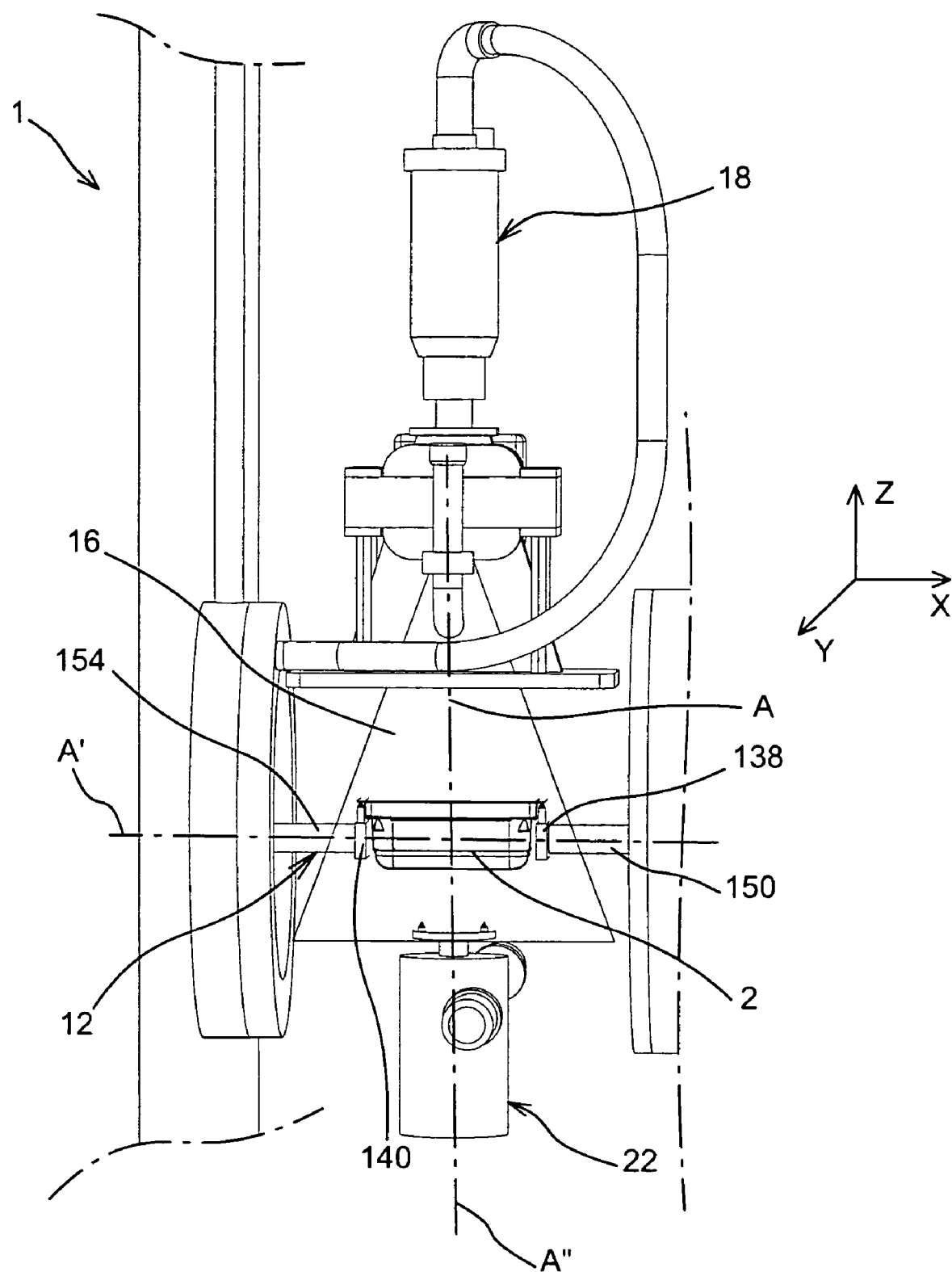
FIG. 7 shows a partial perspective view of an installation for sterilising objects by low-energy electron bombardment, according to another preferred embodiment of the present invention.

In reference to FIG. 7, an installation 1 for sterilising objects 2 by low-energy electron bombardment can be seen, which installation 1 is shown in another preferred embodiment of the present invention.

A number of differences can be seen with respect to the embodiment shown in FIGS. 1 to 6b, and described above. First, it is noted that a major difference lies in the fact that the sterilisation means 18 are pivotally mounted about axis A', by means of a first mechanical module (not referenced). Indeed, during the low-energy electron bombardment treatment, it is the sterilisation means 18 that rotate about axis A' around the object 2 which remains stationary.

In addition, this axis A' still remains the axis according to which the object 2 is capable of being moved in translation inside the installation 1. This is achieved by two substantially coaxial arms 150, 154 each bearing a gripping surface 138, 140 intended to contact the two opposite surfaces YZ of the object 2, respectively, as can be seen in FIG. 7. The two arms 150, 154 are therefore each capable of sliding in direction X with the assistance of means similar to those shown in the embodiment described above, and each of them is mounted on one side of the installation, for example, on the inlet lock 10 and on the outlet lock 24, respectively.

In addition, although it is not shown, the inlet and outlet elevators can be removed, which would then mean that the inlet and outlet conveyors (not shown in FIG. 7) directly and respectively lead to the inlet and outlet locks (not shown in FIG. 7) of the installation 1. In such a case, these conveyors form a baffle so as to provide biological protection.

It is specified that each of the differences mentioned above can be applied to the installation 1 of the embodiment shown in FIGS. 1 to 6b, without going beyond the scope of the invention.

Of course, a variety of modifications can be made by a person skilled in the art to the installation 1 and the method for the sterilisation of objects, which have just been described solely by way of non-limiting examples.

The invention claimed is:

1. An installation for sterilising objects by low-energy electron bombardment on the external surface of said objects, said installation comprising:
   a treatment chamber for receiving an object to be subjected to a sterilisation;
   sterilisation means for sterilising said object with a low-energy electron beam generated by said sterilisation means along a first axis passing through said treatment chamber;
   a first mechanical module for generating, during the sterilisation of the object, a relative rotation movement between the object and said sterilisation means, about a second axis such that the first axis of said electron beam generated by said sterilisation means continuously passes through an external surface of the object during the relative rotation movement about said second axis; and
   a second mechanical module for generating, after the object located inside said treatment chamber is released from the first mechanical module, a rotation of the object about a third axis oriented orthogonally with respect to the second axis.

2. An installation for sterilising objects according to claim 1, wherein said first mechanical module is controlled so as to cooperate, during the sterilisation of the object to be treated located inside said treatment chamber, with any one of two elements selected from said object and said sterilisation means so as to cause said one element to rotate about said second axis.

3. An installation for sterilising objects according to claim 2, wherein the object to be treated constitutes said one element configured to cooperate with the first mechanical module so as to be moved in rotation about said second axis, and wherein said sterilisation means are mounted stationarily on the installation.

4. An installation for sterilising objects according to claim 3, wherein said object has a substantially rectangular parallelepiped shape.

5. An installation for sterilising objects according to claim 4, wherein said first mechanical module is provided with gripping means for gripping the object to be treated, wherein said first module comprises first movement means for bringing said object cooperating with the gripping means, into the treatment chamber so that a first surface of said object is passed through by the first axis, wherein the first mechanical module also includes second movement means for rotating the object and the gripping means about the second axis oriented orthogonally with respect to the first axis and with respect to a second surface of the object, and wherein the second mechanical module includes third movement means for rotating the object released from the gripping means at approximately 90°, inside the treatment chamber, about the third axis oriented orthogonally with respect to the second axis and with respect to any one of the surfaces of the object which are perpendicular to the said second surface.

6. An installation for sterilising objects according to claim 5, wherein said second mechanical module comprises fourth movement means for moving said object in translation according to the third axis, so as to distance said object from said gripping means during a rotation of said object at about 90° about said same third axis caused by the third movement means.

7. An installation for sterilising objects according to claim 6, wherein said first mechanical module is designed and controlled so that its gripping means re-engage the object having a substantially rectangular parallelepiped shape which has been moved in rotation at about 90° by the third movement means, SO that said object can be moved in rotation about the axis by the second movement means.

8. An installation for sterilising objects according to claim 7, wherein said third axis is oriented in the direction of the height (Z) of the installation, and wherein said first axis is oriented in the direction of forward movement of the objects (X) in the installation, which directions (X) and (Z) are mutually orthogonal.

9. An installation for sterilising objects according to claim 8, wherein said first axis is also oriented in the direction of the height (Z) of the installation.

10. An installation for sterilising objects according to claim 8, further comprising an inlet lock and an outlet lock containing therebetween said treatment chamber communicating with said inlet and outlet locks, which treatment chamber as well as the two inlet and outlet locks are aligned in said direction (X).

11. An installation for sterilising objects according to claim 10, wherein said first movement means are designed so as to allow for a translation movement in direction (X) of the object held by the gripping means, between the inlet lock and the treatment chamber, as well as between the latter and the outlet lock.

12. An installation for sterilising objects according to claim 10, wherein the two inlet and outlet locks in a closed position, and said treatment chamber, jointly form an unsealed, shielded enclosure.

13. An installation for sterilising objects according to claim 10, wherein each of the two inlet and outlet locks is associated with an elevator oriented in the direction (Z).

14. An installation for sterilising objects according to claim 13, wherein each of the two elevators comprises a shielded mobile plate serving as a carrier for the object, which shielded mobile plate is designed so as to ensure the closure of the lock with which it is associated.

15. An installation for sterilising objects according to claim 13, wherein the two elevators cooperate respectively with an inlet conveyor and an outlet conveyor, each capable of moving said objects.

16. An installation for sterilising objects according to claim 15, wherein said outlet conveyor leads to a production isolator into which the sterilised objects are delivered.

17. An installation for sterilising objects according to claim 10, wherein said first mechanical module is mounted stationarily on said inlet lock.

18. An installation for sterilising objects according to claim 1, wherein the sterilisation means include an electron gun mounted at the periphery of said treatment chamber.

19. An installation for sterilising objects according to claim 1, wherein said sterilisation means for sterilising generates said low-energy electron beam at an energy level that is sufficient to sterilize medical devices.

20. An installation for sterilising objects according to claim 1, wherein said sterilisation means for sterilising generates said low-energy electron beam at an energy level that is at least 200 KeV and less than 400 KeV.

21. An installation for sterilising objects according to claim 1, wherein said first mechanical module generates said relative rotation movement between the object and the sterilisation means about the second axis over a range of at least 360°.

22. An installation for sterilising objects according to claim 1, wherein said sterilisation means regulates a dose of energy received by said object from said low-energy electron beam during said relative rotation movement so that, after said relative rotation movement, each surface of said object exposed to said low-energy electron beam during said relative rotation movement has received a substantially identical and uniform dose of energy from said low-energy electron beam.

23. An installation for sterilising objects according to claim 22, wherein said sterilisation means regulates said dose of energy received by said object by varying a power of said low-energy electron beam during said relative rotation movement.

24. An installation for sterilising objects according to claim 22, wherein said sterilisation means regulates said dose of energy received by said object by controlling a position of said sterilisation means relative to said object.

25. An installation for sterilising objects according to claim 1, wherein said first mechanical module does not generate any movement of said object during said rotation of the object about the third axis generated by the second mechanical module.

26. An installation for sterilising objects according to claim 1, further comprising shielding means for providing total biological protection from said low-energy electron beam generated by said sterilisation means during said sterilisation.

27. An installation for sterilising objects according to claim 26, wherein said shielding means comprise a protective double-wall with an impervious coating of stainless steel and a shielded coating of lead.

\* \* \* \* \*